United States Patent
Parker et al.

(10) Patent No.: US 8,492,150 B2
(45) Date of Patent: Jul. 23, 2013

(54) ENGINEERED CELL GROWTH ON POLYMERIC FILMS AND BIOTECHNOLOGICAL APPLICATIONS THEREOF

(75) Inventors: Kevin Kit Parker, Cambridge, MA (US); Adam W. Feinberg, Cambridge, MA (US); George M. Whitesides, Newton, MA (US); Sergey S. Shevkoplyas, New Orleans, LA (US); Alexander Feigel, Petah-Tikva (IL)

(73) Assignee: President and Fellows of Harvard College, Cambridge, MA (US)

( * ) Notice: Subject to any disclaimer, the term of this patent is extended or adjusted under 35 U.S.C. 154(b) by 1157 days.

(21) Appl. No.: 12/223,560

(22) PCT Filed: Feb. 5, 2007

(86) PCT No.: PCT/US2007/003051
§ 371 (c)(1), (2), (4) Date: Feb. 25, 2009

(87) PCT Pub. No.: WO2008/051265
PCT Pub. Date: May 2, 2008

(65) Prior Publication Data
US 2009/0317852 A1    Dec. 24, 2009

Related U.S. Application Data

(60) Provisional application No. 60/764,905, filed on Feb. 3, 2006, provisional application No. 60/828,941, filed on Oct. 10, 2006.

(51) Int. Cl.
*C12N 5/07* (2010.01)
(52) U.S. Cl.
USPC .......................................... 435/402; 435/395
(58) Field of Classification Search
None
See application file for complete search history.

(56) References Cited

U.S. PATENT DOCUMENTS

| | | |
|---|---|---|
| 6,821,107 B1 | 11/2004 | Hara et al. |
| 2003/0134331 A1 | 7/2003 | Marks et al. |
| 2004/0009566 A1 | 1/2004 | Okano et al. |
| 2004/0048239 A1 | 3/2004 | Farinas et al. |
| 2004/0078090 A1 | 4/2004 | Binette et al. |
| 2004/0101819 A1* | 5/2004 | Montemagno et al. ............ 435/4 |
| 2005/0080402 A1 | 4/2005 | Santamore et al. |
| 2005/0085847 A1 | 4/2005 | Galdonik et al. |
| 2006/0003439 A1 | 1/2006 | Ismagilov et al. |
| 2006/0134692 A1 | 6/2006 | Emmert-Buck et al. |
| 2007/0053996 A1 | 3/2007 | Boyden et al. |
| 2009/0023773 A1 | 1/2009 | Vohra et al. |

FOREIGN PATENT DOCUMENTS

| | | | |
|---|---|---|---|
| EP | 0387975 | | 9/1990 |
| EP | 1302535 | | 4/2003 |
| WO | WO2004/014212 | | 2/2004 |
| WO | WO2006/068972 | | 6/2006 |
| WO | WO 2008/045506 | * | 4/2008 |
| WO | WO2010/127280 | | 11/2010 |

OTHER PUBLICATIONS

Yang et al., "fabrication of well-defined PLGA scaffolds using novel microembossing and carbon dioxide bonding", Biomaterials, 2005, vol. 26, pp. 2585-2594.*
Xi et al., "Development of a Self-Assembled Muscle-Powered Piezoelectric Microgenerator", NSTI-Nanotech, 2004, vol. 1, pp. 3-6.*
Alford, P.W., et al., "Biohybrid Thin Films for Measuring Contractility in Engineered Cardiovascular Muscle." Biomaterials. 2010, 31: 3613-3621.
Bol, M., et al. "Computational modeling of muscular thin films for cardiac repair." Computational Mechanics. Sep. 13, 2008;43(4):535-44.
Bray M.A., et al. "Sarcomere alignment is regulated by myocyte shape." Cell Motil Cytoskeleton. Aug. 2008;65(8):641-51.
Bursac, N., et al. "Cardiomyocyte cultures with controlled macroscopic anisotropy: a model for functional electrophysiological studies of cardiac muscle." Circ Res. Dec. 13, 2002;91(12):e45-54.
Feinberg, A.W., et al. "Muscular thin films for building actuators and powering devices." Science. Sep. 7, 2007;317(5843):1366-70.
Geisse, N.A., et al. "Micropatterning Approaches for Cardiac Biology." In: Khademhosseini A, Toner M, Borenstein JT, Takayama S, editors. Micro- and Nanoengineering of the Cell Microenvironment: Technologies and Applications. Boston: Artech House; 2008, p. 341-357.
Park J et al: "Real-time measurement of 17,18 the contractile forces of self-organized cardiomyocytes on hybrid biopolymer microcantilevers", Analytical Chemistry, American Chemical Society, US,vo 1. 77, No. 20, Oct. 15, 2005.
Parker, K.K. ,et al. "Myofibrillar architecture in engineered cardiac myocytes." Circ Res. Aug. 15, 2008;103(4):340-2.

* cited by examiner

Primary Examiner — Laura Schuberg
(74) Attorney, Agent, or Firm — McCarter & English, LLP; Maria Laccotripe Zacharakis; Deborah L. Nagle

(57) ABSTRACT

A free-standing thin film is fabricated from a structure comprising a base layer coated with a sacrificial polymer layer, which is in turn coated with a flexible polymer layer. Cells are then seeded onto the flexible polymer layer and cultured to form a tissue. The flexible polymer layer is then released from the base layer to produce a free-standing thin film comprising the tissue on the flexible polymer layer. In one embodiment, the cells are myocytes, which can be actuated to propel or displace the free-standing film. In another embodiment, the free-standing film is used to treat injured human tissue.

32 Claims, 11 Drawing Sheets

ENGINEERED CELL GROWTH ON POLYMERIC FILMS AND BIOTECHNOLOGICAL APPLICATIONS THEREOF

GOVERNMENT SUPPORT

This invention was made with government support under FA9550-01-1-0015 awarded by the U.S. Air Force Office of Scientific Research and W911NF-04-1-0170 awarded by the U.S. Army Research Laboratory. The United States Government has certain rights in the invention.

BACKGROUND

In nature, living cells divide and interconnect in the formation of complex biological systems creating structure-function hierarchies that span from the micrometer to meter scales. This bottom-up approach leverages genetic programming and environmental stimuli to direct cellular self-assembly and organogenesis into specialized tissues and organs. Capabilities including the parallel processing of neural networks, the combination of force, strain and efficiency of striated muscle and the immune response to pathogens far exceeds what can be achieved in manmade systems. Learning to use living cells as an integral building block in manmade, synthetic systems thus portends the ability to create classes of hybrid devices that combine the advantages of biological and engineering grade materials. Efforts to build biosynthetic materials or engineered tissues that recapitulate these structure-function relationships often fail because of the inability to replicate the in vivo conditions that coax this behavior from ensembles of cells. For example, engineering a functional muscle tissue requires that the sarcomere and myofibrillogenesis be controlled at the micron length scale, while cellular alignment and formation of the continuous tissue require organizational cues over the millimeter to centimeter length scale. Thus, to build a functional biosynthetic material, the biotic-abiotic interface must contain the chemical and mechanical properties that support multiscale coupling.

SUMMARY

Described herein are robust, intrinsically contractile biosynthetic materials actuated by ensembles of molecular motors. The ensembles include one or an array of muscle cells, e.g., skeletal muscle cells, smooth muscle cells, or cardiac muscle cells. Alternatively, the mixtures of cells, e.g., muscle cells and neuronal cells, are used.

Striated muscle cells include skeletal and cardiac muscle. In nature, striated muscle tissue utilizes high-density arrays of actin-myosin motor complexes organized into contractile subunits, termed, sarcomeres, which assemble serially into myofibrils that span the length of cardiomyocytes and skeletal myoblasts. These muscle cells supply energy for the motor proteins by converting glucose into ATP and controlling excitation-contraction coupling by regulating $Ca^{2+}$ concentration. Based on these properties, myocytes have been exploited as a single-cell linear actuator. These actuators are used to synchronize the actuation of motor proteins by interconnecting to form a mechanically and electrically continuous two-dimensional (2D) muscular tissue, such as myocardium. Free-standing, surface-modified thin films formed, e.g., of polydimethylsiloxane (PDMS), support the myocyte self assembly of serially aligned sarcomeres and the parallel bundling of myofibrils using patterned extracellular-matrix (ECM) proteins. While the myocytes provide contractile function, the polydimethylsiloxane thin film provides restorative elasticity and improved handling characteristics. Specifically, the polydimethylsiloxane film thickness dictates muscle sheet bending stiffness, while the structural integrity of the polydimethylsiloxane film allows the muscle sheet to be formed into near any planar shape without disrupting the 2D myocyte tissue.

These constructs, which are termed, muscular thin films (MTF), are engineered for desired functionalities. For example, specific embodiments include soft robotic actuators and semi-autonomous, motile constructs that swim or walk autonomously or under external electrical stimulation or both. Spatially organized sarcomeres act as efficient linear actuators that have inherent control systems for regulating contraction initiation and propagation. Shortening of myocytes during synchronous, coordinated contraction causes the polydimethylsiloxane thin film to bend during systole and return to its original shape during diastole. The desired performance characteristics of the muscular thin film can be obtained by engineering the size, shape, thickness, tissue microarchitecture and pacing of actuation. In one example, these variables are manipulated to obtain the desired velocity of a swimmer. Furthermore, the spatial and temporal symmetry break utilized herein to generate directed motility in a semi-autonomous swimmer serve as a model for biomimetic anguilliform locomotion. Based on these examples, muscular thin films are useful in prosthetics, tissue engineering, muscle powered microdevices, bench top drug analysis and mechanical and chemical sensors.

A method for measuring the contractility of a muscle is carried out by providing a muscular thin film comprising a flexible polymer layer coated with the muscle; attaching or clamping an end of the muscular thin film to a mounting structure; applying a stimulus to cause the muscle to contract; and measuring the displacement of the muscular thin film when the muscle is contracted. Measuring the displacement of the film is carried out by detecting a change in a radius of curvature of the muscular thin film when the muscle is contracted compared to when it is relaxed as well as measuring the rate of contraction. The methods are useful to screen for candidate compounds for drugs that promote contraction (e.g., vasocontraction) or relaxation (e.g., vasodilation) for drugs that treat or reduce the severity of disorders that are characterized by aberrant muscular activity (e.g., excessive contraction, excession relaxation, disregulation of contractile function (e.g., heart arrhythmia or vasospasms)). For example, the muscle cells are contact with a candidate compound prior to applying a contractile stimulus and the degree of contraction or the rate of contraction in the presence of the candidate compound is measured and compared relative to displacement in the absence of the candidate compound. The cells on the film are normal wild type cells, diseased cells, physically-damaged cells, or genetically altered cells. A difference between the degree of or rate indicates that the candidate compound alters muscular function, i.e., increases contractile function or decreases contractile function.

In other embodiments, neurons, fibroblasts, endothelial cells, smooth muscle cells or skin cells are used in place of muscle cells. The cells are functionally active, meaning that the attached cells perform at least one function of that cell type in its native environment. For example, a myocyte cell contracts, e.g., a cardiomyocyte cell contracts with particular direction along a single axis. Neural cells transduce or transmit an electrical signal to another neural cell. The neurons are used, e.g., for signal propagation. The fibroblasts are used for ECM deposition. The endothelial cells are used for construction or repair of blood vessels. The smooth muscle cells are used for slow, tonic contractions.

One use of the engineered tissue structures described herein is to repair and/or reinforce the corresponding tissue in a mammal, e.g., an injured or diseased human subject. For example, the cell-seeded films/polymers are use as or in prosthetic devices, tissue implants, and wound dressing. Such wound dressing offer improved healing of lesions that are often difficult to treat, e.g., burns, bedsores, and abrasions. The structures are also useful to repair other tissue defects, e.g., for organ repair due to birth defects such as gastroschisis or defects due to degenerative diseases. Wound dressing compositions are portable and amenable to both hospital (e.g., operating room) use as well as field (e.g., battlefield) use.

Figure 1:
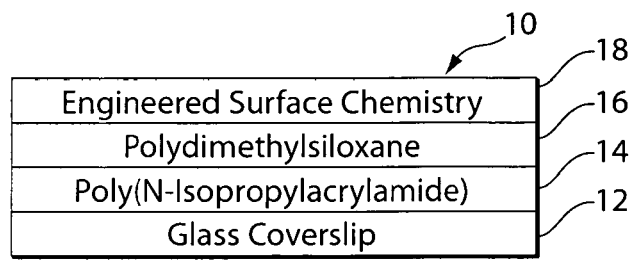
FIGS. 1-5 depict a schematic of fabrication steps that may be used to make free-standing films functionalized with cells and/or proteins.

The foregoing and other features and advantages of the invention will be apparent from the following, more-particular description. In the accompanying drawings, like reference characters refer to the same or similar parts throughout the different views. The drawings are not necessarily to scale, emphasis instead being placed upon illustrating particular principles, discussed below.

DETAILED DESCRIPTION

Figure 2:
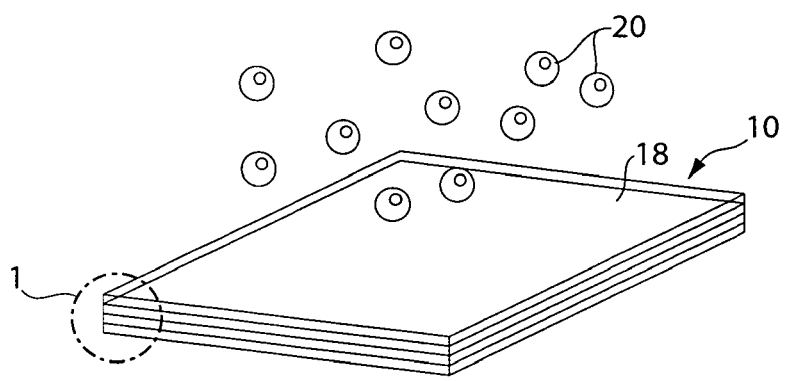
Figure 3:
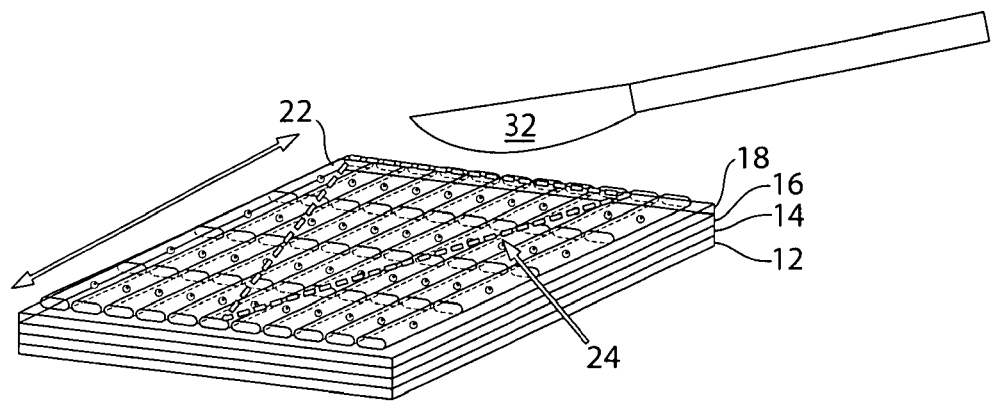
Figure 4:
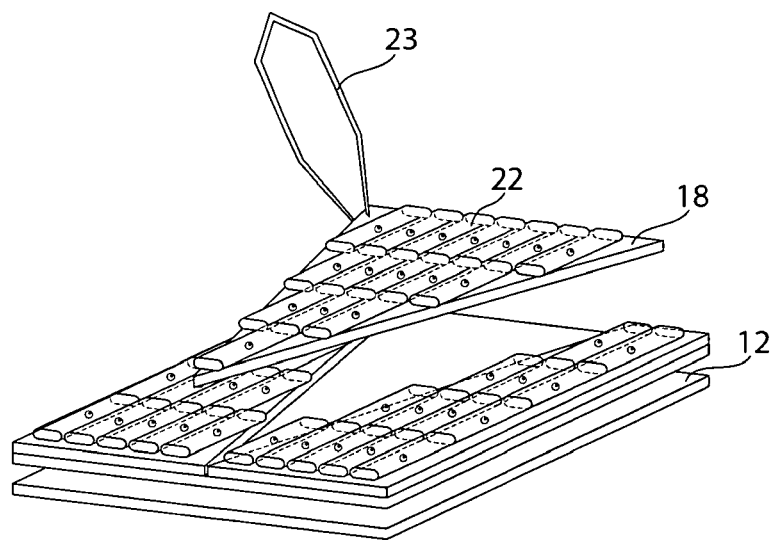

Schematic representations of fabrication steps used to make free-standing films functionalized with cells and/or proteins for biotechnology applications are provided in FIGS. 1-5. As shown in FIG. 1, the substrates 10 are fabricated as a rigid base material 12 coated with a sacrificial polymer layer 14; a flexible polymer layer 16 is temporarily bonded to the rigid base material 12 via the sacrificial polymer layer 14, and an engineered surface chemistry 18 is provided on the flexible polymer layer 16 to enhance or inhibit cell and/or protein adhesion. Cells 20 are seeded onto the flexible polymer layer 18, as shown in FIG. 2, and cultured to form a tissue 22 comprising, in this embodiment, patterned anisotropic myocardium. A desired shape 24 of the flexible polymer layer can then be cut, as shown in FIG. 3; and the flexible film, including the polymer layer 16 and tissue 22, can be peeled off with a pair of tweezers 23 as the sacrificial polymer layer 14 dissolves to release the flexible polymer layer 16, as shown in FIG. 4, to produce the free-standing film 26 shown in FIG. 5, which can then be actuated or further modified.

The base material 12 is formed of a rigid or semi-rigid material, such as a metal, ceramic or polymer having an elastic modulus greater than, for example, 1 MPa. Examples of suitable substrates include a glass cover slip, polyethylene terephthalate film, silicon wafer, etc. In one embodiment, the base material is a glass cover slip coated with a sacrificial polymer layer formed of poly(N-Isopropylacrylamide) (PIPAAM). The sacrificial polymer layer 14 is applied to the rigid base material 12 via spin coating, dip casting, spraying, etc., wherein the base material 12 is mounted to a chuck under vacuum and is rotated to spin the base about its axis of symmetry; and the polymer is dripped onto the base 12, with the centrifugal force generated by the spin causing the liquid polymer to spread substantially evenly across the surface of the base 12. The resulting sacrificial polymer layer 14 serves to temporarily secure additional coatings that are subsequently formed thereon.

In one embodiment, the sacrificial polymer is a thermally sensitive polymer that is melted or dissolved to cause the release of the flexible polymer layer 16. An example of such a polymer is linear, non-cross-linked poly(N-Isopropylacrylamide), which is a solid when dehydrated, and which is a solid at 37° C. (wherein the polymer is hydrated but relatively hydrophobic). However, when the temperature is dropped to 32° C. or less (where the polymer is hydrated but relatively hydrophilic), the polymer becomes a liquid, thereby releasing the flexible polymer layer 16.

In another embodiment, the sacrificial polymer becomes hydrophilic, thereby releasing hydrophobic coatings, with a change in temperature. For example, the sacrificial polymer can be hydrated, crosslinked N-Isopropylacrylamide, which is hydrophobic at 37° C. and hydrophilic at 32° C.

In yet another embodiment, the sacrificial polymer is an electrically actuated polymer that becomes hydrophilic upon application of an electric potential to thereby release a hydrophobic structure coated thereon (e.g. PDMS as the flexible polymer layer). Examples of such a polymer include poly (pyrrole)s, which are relatively hydrophobic when oxidized and hydrophilic when reduced. Other examples of polymers that can be electrically actuated include poly(acetylene)s, poly(thiophene)s, poly(aniline)s, poly(fluorene)s, poly(3-hexylthiophene), polynaphthalenes, poly(p-phenylene sulfide), and poly(para-phenylene vinylene)s, etc.

In still another embodiment, the sacrificial polymer is a degradable biopolymer that can be dissolved to release a structure coated thereon. In one example, the polymer (e.g., polylactic acid, polyglycolic acid, poly(lactic-glycolic) acid copolymers, nylons, etc.) undergoes time-dependent degradation by hydrolysis. In another example, the polymer undergoes time-dependent degradation by enzymatic action (e.g., fibrin degradation by plasmin, collagen degradation by collagenase, fibronectin degradation by matrix metalloproteinases, etc.).

The sacrificial polymer layer 14 provides temporary adhesion of the base material 12 to a flexible polymer layer 16; the flexible polymer layer 16 is likewise applied, e.g., via spin coating. Traces of the sacrificial polymer layer 14 may be detected on the flexible polymer layer 16 after removal therefrom. Examples of the elastomers that can be used to form the flexible polymer layer 16 include polydimethylsiloxane (PDMS) and polyurethane. In other embodiments, thermoplastic or thermosetting polymers are used to form the flexible polymer layer 16. Alternative non-degradable polymers include polyurethanes, silicone-urethane copolymers, carbonate-urethane copolymers, polyisoprene, polybutadiene, copolymer of polystyrene and polybutadiene, chloroprene rubber, Polyacrylic rubber (ACM, ABR), Fluorosilicone Rubber (FVMQ), Fluoroelastomers, Perfluoroelastomers, Tetrafluoro ethylene/propylene rubbers (FEPM) and Ethylene vinyl acetate (EVA). In still other embodiments, biopolymers, such as collagens, elastins, and other extracellular matrix proteins, are used to form the flexible polymer layer 16**. Suitable biodegradable elastomers include hydrogels, elastin-like peptides, polyhydroxyalkanoates and poly(glycerol-sebacate). Suitable non-elastomer, biodegradable polymers include polylactic acid, polyglycolic acid, poly lactic glycolic acid copolymers.

The thickness of a polydimethylsiloxane flexible polymer layer 16 may be controlled by the viscosity of the PDMS prepolymer and by the spin coating speed, ranging from 14 to 60 μm thick after cure. After mixing the polydimethylsiloxane prepolymer, its viscosity begins to increase as the cross-link density increases. This change in viscosity between mixing (0 hours) and gelation (9 hours) is utilized to spin coat different thickness polydimethylsiloxane films. Following spin coating, the polydimethylsiloxane films are either fully cured at room temperature (about 22° C.), or at 65° C.

The flexible polymer layer 16 is then uniformly or selectively patterned with engineered surface chemistry 18 to elicit (or inhibit) specific cell growth and function. The engineered surface chemistry 18 can be provided via exposure to ultraviolet radiation or ozone or via acid or base wash or plasma treatment to increase the hydrophilicity of the surface. In other embodiments, the surface chemistry 18 can be selected from the following groups:

(a) extracellular matrix proteins to direct cell adhesion (e.g., collagen, fibronectin, laminin, etc.);
(b) growth factors to direct cell function specific to cell type (e.g., nerve growth factor, bone morphogenic proteins, vascular endothelial growth factor, etc.);
(c) lipids, fatty acids and steroids (e.g., glycerides, non-glycerides, saturated and unsaturated fatty acids, cholesterol, corticosteroids, sex steroids, etc.);
(d) sugars and other biologically active carbohydrates (e.g., monosaccharides, oligosaccharides, sucrose, glucose, glycogen, etc.);
(e) combinations of carbohydrates, lipids and/or proteins, such as proteoglycans (protein cores with attached side chains of chondroitin sulfate, dermatan sulfate, heparin, heparan sulfate, and/or keratan sulfate); glycoproteins [e.g., selecting, immunoglobulins, hormones such as human chorionic gonadotropin, Alpha-fetoprotein and Erythropoietin (EPO), etc.]; proteolipids (e.g., N-myristoylated, palmitoylated and prenylated proteins); and glycolipids (e.g., glycoglycerolipids, glycosphingolipids, glycophosphatidylinositols, etc.);
(f) biologically derived homopolymers, such as polylactic and polyglycolic acids and poly-L-lysine;
(g) nucleic acids (e.g., DNA, RNA, etc.);
(h) hormones (e.g., anabolic steroids, sex hormones, insulin, angiotensin, etc.);
(i) enzymes (types: oxidoreductases, transferases, hydrolases, lyases, isomerases, ligases; examples: trypsin, collagenases, matrix metalloproteinases, etc.);
(j) pharmaceuticals (e.g., beta blockers, vasodilators, vasoconstrictors, pain relievers, gene therapy, viral vectors, anti-inflammatories, etc.);
(k) cell surface ligands and receptors (e.g., integrins, selectins, cadherins, etc.);
(l) cytoskeletal filaments and/or motor proteins (e.g., intermediate filaments, microtubules, actin filaments, dynein, kinesin, myosin, etc.); and
(m) hydrophylic polymers (e.g., polyethylene oxide or pluronics) are applied to decrease or prevent cell/protein adhesion.

These changes in surface chemistry may be uniform across the surface or patterned spatially (e.g., with features having dimensions ranging from 5, 10, 20, 50, 100 nanometers to 1-1,000 micrometers to the larger macroscale) using a technique, such as, but not limited to, soft lithography, self assembly, vapor deposition and photolithography. Each of these techniques is discussed, in turn, below.

a) Soft Lithography

In soft lithography, structures (particularly those with features measured on the scale of 1 nm to 1 μm) are fabricated or replicated using elastomeric stamps, molds, and conformable photomasks. One such soft lithography method is microcontact printing using a polydimethylsiloxane stamp. Microcontact printing has been realized with fibronectin and can be extended to other extracellular matrix proteins including, but not limited to laminin, collagens, fibrin, etc. Other biopolymers can be used as well, as this soft lithography method is quite versatile. There are few, if any, limitations on the geometry of the biopolymer structure(s) beyond the types of patterns that can be created in the polydimethylsiloxane stamps used for microcontact printing. The range of patterns in the stamps, in turn, spans across those obtainable with the current microprocessing technology used in the manufacture of integrated circuits. As such, available designs encompass nearly anything that can be drafted in modern computer-aided-design software. Multiple layers of biopolymers can be printed on top of one another using the same or different stamps with the same or different proteins to form an integrated polyprotein (poly-biopolymer) layer on top of the flexible polymer layer 16, which can subsequently be released and used.

b) Self Assembly

Various biopolymers will spontaneously form self-assembled structures. Examples, without limitation, of self assembly include assembly of collagen into fibrils, assembly of actin into filaments and assembly of DNA into double strands and other structures depending on base-pair sequence. The self assembly can be directed to occur on the flexible polymer layer 16 to create a nanometer-to-millimeter-scale spatially organized biopolymer layer. Further, self assembly can be combined with soft lithography to create a self-assembled layer on top of a soft-lithographically patterned biopolymer; alternatively, the processes can be carried out in the reverse order. The self-assembled biopolymer, depending on the strength and stability of intermolecular forces, may or may not be stabilized using a cross-linking agent (for example, glutaraldehyde, formaldehyde, paraformaldehyde, etc.) to maintain integrity of the biopolymer layer on the flexible polymer layer 16. Otherwise, existing intermolecular forces from Van der Walls interactions, hydrogen binding, hydrophobic/hydrophilic interactions, etc., may be strong enough to hold the biopolymer scaffold together on the flexible polymer layer 16.

c) Vapor Deposition

Using a solid mask to selectively control access to the surface of the flexible polymer layer 16, biopolymers can be deposited in the accessible regions via condensation from a vapor phase. To drive biopolymers into a vapor phase, the deposition is performed in a controlled environmental chamber where the pressure can be decreased and the temperature increased such that the vapor pressure of the biopolymer approaches the pressure in the environmental chamber. Biopolymer surfaces produced via vapor deposition can be combined with biopolymer surfaces created by self-assembly and/or by soft lithography.

d) Patterned Photo-Cross-Linking

Patterned light, x-rays, electrons or other electromagnetic radiation can be passed through a mask by photolithography; alternatively, the radiation can be applied in the form of a focused beam, as in stereolithography, to control where on the flexible polymer layer 16 biopolymers attach. Photolithography can be used with biopolymers that intrinsically photo-cross-link or that change reactivity via the release of a photoliable group or via a secondary photosensitive compound to promote cross-linking or breaking of the polymer chains so that the surface areas that are exposed to light are rendered either soluble or insoluble to a developing solution that is then applied to the exposed biopolymer to leave only the desired pattern intact. The biopolymer is provided in an aqueous solution of biopolymer intrinsically photosensitive or containing an additional photosensitive compounds.

Examples of photo-cross-linking processes that can be utilized include (a) ultra-violet photo-cross-linking of proteins to RNA [as described in A. Paleologue, et al., "Photo-Induced Protein Cross-Linking to 5S RNA and 28-5.8S RNA within Rat-Liver 60S Ribosomal Subunits," Eur. J. Biochem. 149, 525-529 (1985)]; (b) protein photo-cross-linking in mammalian cells by site-specific incorporation of a photoreactive amino acid [as described in N. Hino, et al., "Protein Photo-Cross-Linking in Mammalian Cells by Site-Specific Incorporation of a Photoreactive Amino Acid," Nature Methods 2, 201-206 (2005)]; (c) use of ruthenium bipyridyls or palladium porphyrins as photo-activatable crosslinking agents for proteins [as described in U.S. Pat. No. 6,613,582 (Kodadek et al.)]; and (d) photocrosslinking of heparin to bound proteins via the cross-linking reagent, 2-(4-azidophenylamino)-4-(1-ammonio-4-azabicyclo[2,2,2]oct-1-yl)-6-morpho-lino-1,3,5-triazine chloride [as described in Y. Suda, et al., "Novel Photo Affinity Cross-Linking Resin for the Isolation of Heparin Binding Proteins," Journal of Bioactive and Compatible Polymers 15, 468-477 (2000)].

To attach cells, substrates are placed in culture with a cell suspension allowing the cells 20 to settle and adhere to the surface 18, as shown in FIG. 2. In the case of an adhesive surface treatment, cells bind to the material in a manner dictated by the surface chemistry. For patterned chemistry, cells respond to patterning in terms of growth and function. Examples of cell types that are attached include myocytes (e.g., cardiac myocytes) for muscle-based motion; neurons for electrical-signal propagation; fibroblasts for extra-cellular-matrix propagation; endothelial cells for blood contact; smooth muscle cells for slow, tonic contraction; and skin cells.

Figure 5:
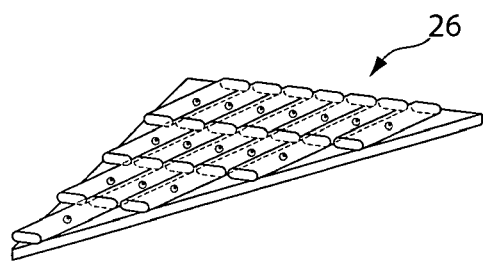

The cells on the substrates are cultured in an incubator under physiologic conditions (e.g., at 37° C.) until the cells form a two-dimensional (2D) tissue (i.e., a layer of cells that is less than 200 microns thick, or, in particular embodiments, less than 100 microns thick, or even just a monolayer of cells), the anisotropy or isotropy of which is determined by the engineered surface chemistry. A specific shape 24 (tailored to the intended application) is cut in the flexible polymer film 16 using a scalpel 32 (as shown in FIG. 3), punch, die or laser. The sacrificial layer 14 is then dissolved or actuated to release the flexible polymer 16 from the rigid base 12 (e.g., by dropping the temperature below 35° C.; and the cut-out shape 24 then floats free or is gently peeled off, as shown in FIG. 4. The free-standing flexible film 26 of desired shape, as shown in FIG. 5, can be modified further by adopting/forming a three-dimensional (3D) conformation and then integrated into a multi-construct device or prepared for use as a tissue engineering/regeneration scaffold for, e.g., the manufacture and use of biologically actuated control devices, bench-top drug analysis, wound dressings, artificial organs, and grafts for repairing soft and hard tissue.

Figure 6A:
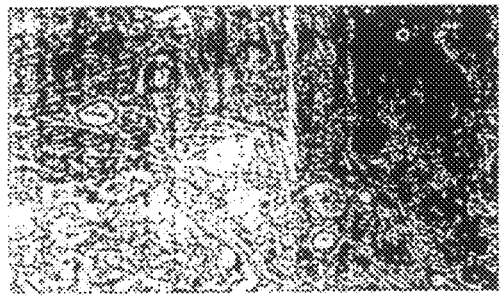
FIG. 6 is a series of images of cardiomyocytes cultured on different uniform and micro-patterned layers of fibronectin to produce 2D myocardium with different microstructures.
Figure 6B:
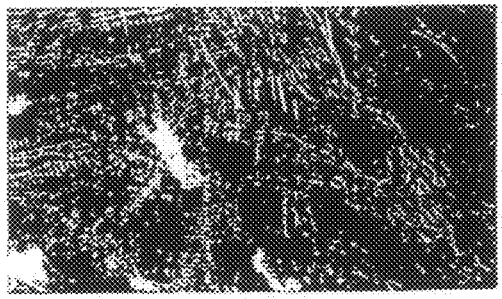
Figure 6C:
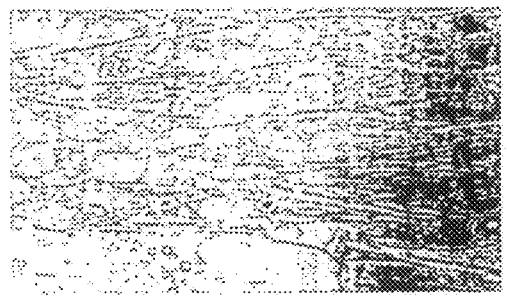
Figure 6D:
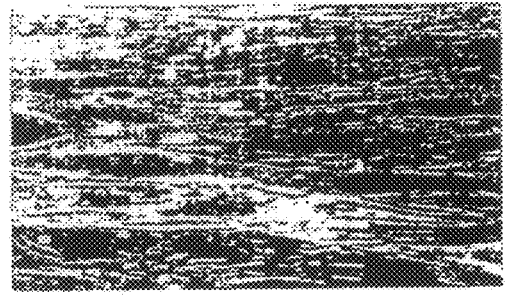
Figure 6E:
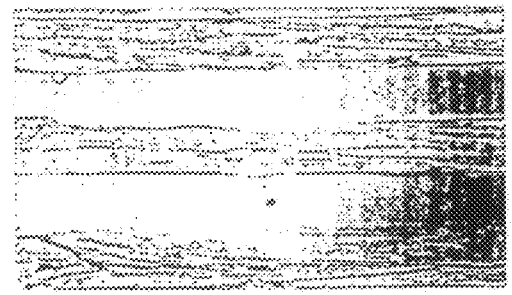
Figure 6F:

In particular embodiments, the extracellular-matrix protein, fibronectin is adsorbed to the polydimethylsiloxane. Cardiomyocytes cultured on different uniform and micropatterned layers of fibronectin produce 2D myocardium with different microstructures. Uniform fibronectin coatings produce isotropic 2D myocardium (as shown in FIGS. 6A and 6B) with no long-range order. Staining for sarcomeric α-actinin reveals no preferential alignment of sarcomeres along any axis. Micropatterns of alternating high and low density 20-μm-wide fibronectin lines (as shown in FIGS. 6C and 6D) produce continuous anisotropic 2D myocardium. Staining for sarcomeric α-actinin reveals uni-axial alignment of sarcomeres along a single axis. Anisotropy of 2D tissue is controlled by the relative concentrations of stamping and background extracellular-matrix protein. Micropatterns of alternating 20-μm-wide lines of high-density fibronectin and Pluronics (as shown in FIGS. 6E and 6F) produce a discontinuous array of anisotropic 1D myocardial strips. These tissue strips are electrically isolated from one another preventing coordinated, spontaneous contraction of an entire muscular thin film. Staining for sarcomeric α-actinin reveals uni-axial alignment of sarcomeres along a single axis. The images represent 10× phase; 63× immunofluorescence of nuclei, F-actin and sarcomeric α-actinin; and the signal from sarcomeric α-actinin alone to emphasize the direction of sarcomere alignment.

In one embodiment, primary neonatal rat ventricular myocytes are seeded onto the fibronectin-coated polydimethylsiloxane and cultured at 37° C. for periods of 3 to 6 days prior to use. The myocytes spontaneously align with the fibronectin, and myofibrillogenesis is cued by the geometry of the patterned extracellular matrix. Adjacent myocytes spontaneously generate mechanical continuity via costameres, and gap junctions form to establish electrical continuity via genetically programmed pathways. Once the myocardium has formed, muscular thin films are removed from the incubator, and the culture media is exchanged for Tyrode's solution to provide the requisite ion and glucose concentrations for prolonged contraction. When cooled to room temperature, the desired muscular-thin-film shape is manually prepared with a scalpel, which concurrently allows the aqueous dissolution of the PIPAAm layer and release of the muscular thin film into solution. Depending on the tissue microarchitecture and muscular-thin-film shape, constructs contract spontaneously or can be controlled more precisely by field stimulation electrodes. Thus, tissue architecture, thin-film shape and thickness, and external pacing achieve designer functionality.

Figure 7:
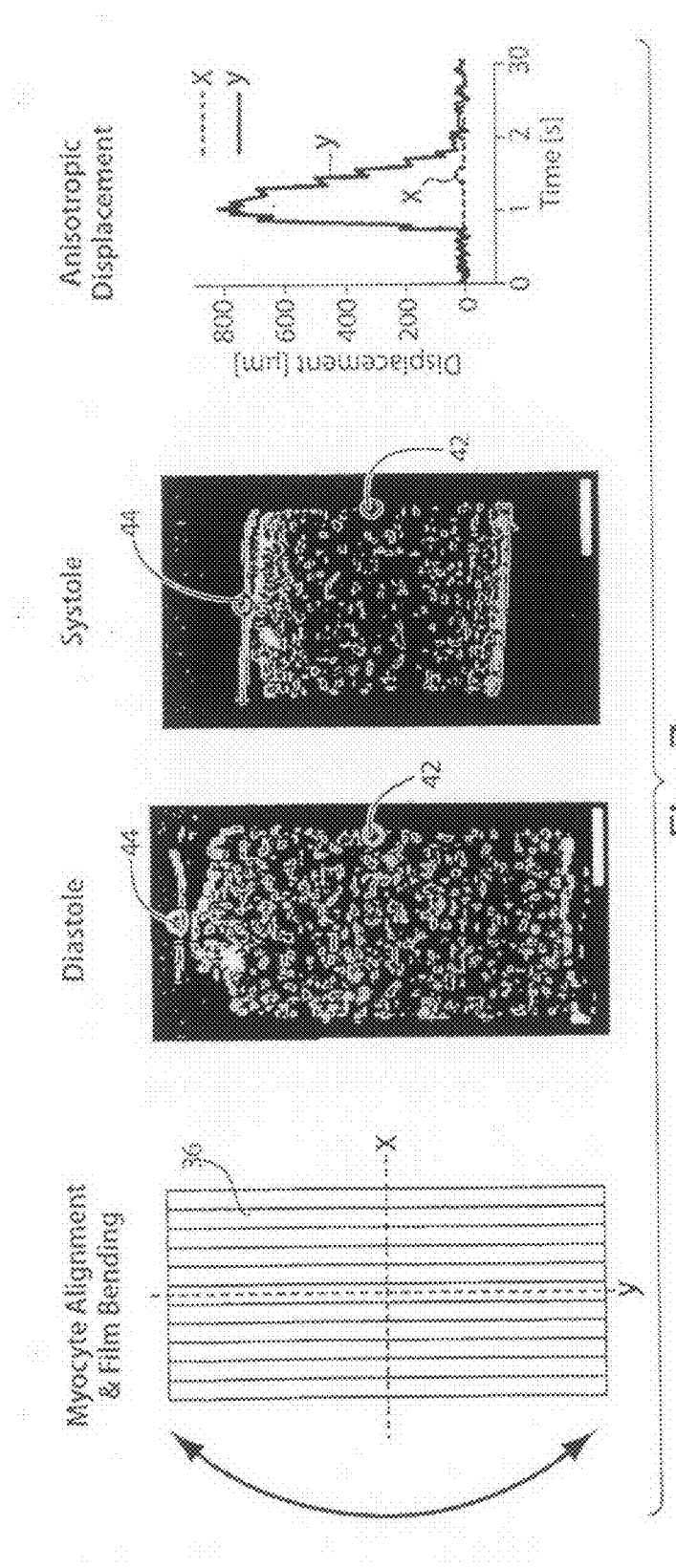
FIG. 7 depicts an example of an asymmetric film shape and tissue anisotropy.

An example of a symmetric film shape and tissue anisotropy that is accessible using the methods disclosed herein is shown in FIG. 7. This construct produces no net displacement yet is applicable as an actuator. The anisotropic 2D tissue defines the main axis of contraction. Deformation upon contraction is additive in the direction of anisotropy and thus is maximized for longer lengths of uninterrupted myofibrils. As shown at left in FIG. 7, the sample is a rectangle 36 with anisotropy parallel to the length, y (i.e., with myocytes aligned along the length, y, of the rectangle 36), wherein a larger uni-axial displacement is evident—in this case, only along the length, y. Myocyte alignment is indicated by the lines, and the ends that bend out of plane during contraction are indicated by arrows. To the right of this schematic are two video stills showing the construct in a relaxed state (under the heading, Diastole) at time 0.00 seconds and in a contracted state (under the heading, Systole) about 0.25 seconds later. Positions tracked are indicated by circles 42 for the x axis and circles 44 for the y axis and plotted for a single contraction in the graph to the right. Scale bars in each of the images are 1 mm.

In this case and in others with different shapes (e.g., square and triangle) and different orientations of myocyte alignment, the muscular thin films contracted along the axis of myocardial alignment only with minimal contraction along the orthogonal axis. The degree of muscular thin film bending is determined by two factors, bending stiffness of the polydimethylsiloxane films and the strength of muscular contraction. For similarly sized rectangles, myocytes aligned along the length, y, contracted about 800 µm (as shown in FIG. 7, graph) while myocytes aligned along the width, x, of a similarly sized rectangle contracted about 175 µm. The bending stiffness of the muscular thin film along any given axis, much like a cantilever, increases with the elastic modulus, thickness and width while decreasing with length.

When released from the cover slip, the polydimethylsiloxane films are no longer restricted by a rigid substrate and are free to adopt 3D conformations. Thicker films, such as those used for the symmetric rectangle, square and triangle examples, only bend out of plane during myocyte contraction. However, thinner films begin to bend as soon as the muscular thin films are released from the cover slips-producing two possible modes of film bending during contraction. Constructs 25' with myocyte on the convex surface (FIG. 8A) contract and bend the film 26' back in plane, increasing (or even inverting) the radius of film curvature. In contrast, constructs 25" and 25''' with myocyte on the concave surface (FIGS. 8B and 8C) contract and bend the film 26" and 26''' further out of plane, decreasing the radius of film curvature. These two different film conformations can be leveraged to engineer a variety of different constructs that increase or decrease film radius of curvature during contraction.

Figure 8C:
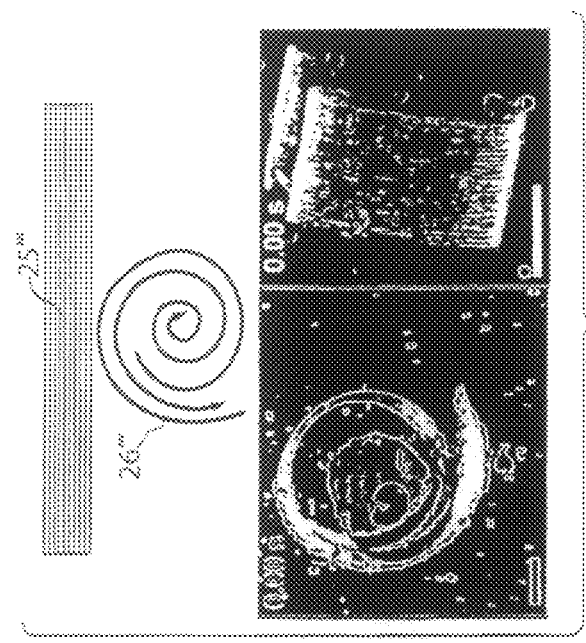
FIG. 8 provides illustrations and images for various embodiments of soft robotic actuators created from muscular thin films.

A wide range of actuators and other devices can be generated with this technology. In one embodiment, helical linear actuators formed from high-aspect-ratio, rectangular thin films 26' with muscle fibers oriented off-axis relative to the film's long axis are capable of cyclic, axial extension and can be angled and counter rotated with variable pitch (as shown in FIG. 8A). Using 65° C.-cured polydimethylsiloxane produces muscular-thin-film constructs that start in a relaxed, nearly flat state and then rollup into a helix upon contraction. As a soft robotic actuator, the transition from a flat rectangle to a 3D helix enables axial displacement and rotation with very simple fabrication steps. Using this system, a variety of 2D shapes can be generated that will fold into intricate 3D shapes. When paced at 0.5 Hz and 20 V, the film strip 26' rotates and lengthens during myocyte contraction, exhibiting systolic extension of about 200 µm coupled with about 55° of rotation.

Figure 8B:
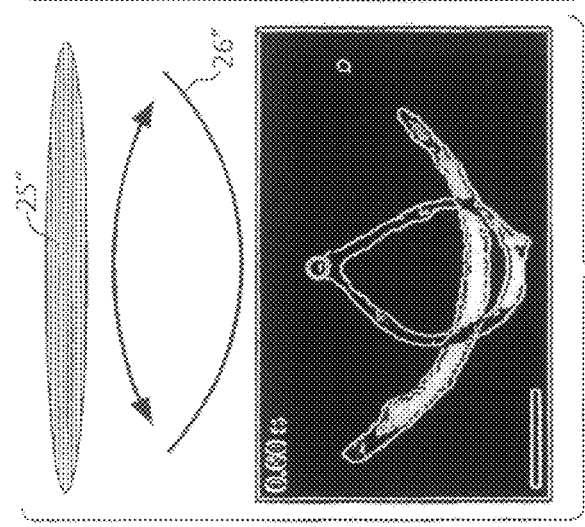
Figure 8A:
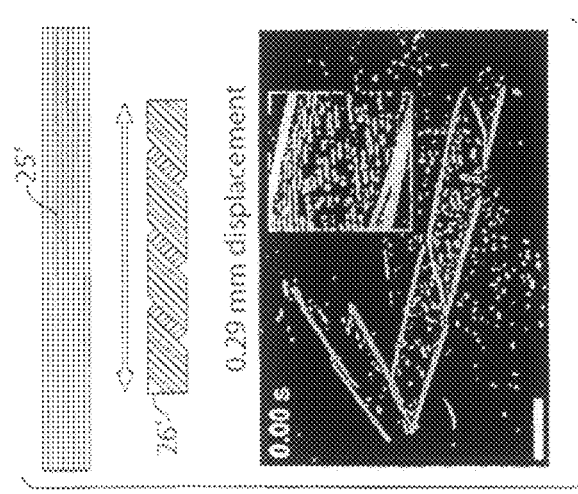

A gripper 26" in the form of a thin rectangular strip is illustrated in FIG. 8B. The gripper 26" has anisotropic myocytes aligned along the length (and on the concave surface) that bring the tips together upon myocyte contraction. During contraction, the ends of the gripper 26" come together until they touch and stop due to the contact force. Rather than simply opening and closing once, the gripper 26" can switched from an open state (diastole) to a closed state (peak systole) by increasing the pacing rate until the 2D myocardium of the muscular thin film enters tetanus. In FIG. 8B, a closed grip is achieved at 5 Hz pacing with intermediated open/closed states between 1 and 2 Hz pacing, thereby demonstrating the ability to control the functionality and temporal state of muscular-thin-film based soft robotic actuators by electrical pacing.

In FIG. 8C, the coiled film strip 26''' is a rectangle with anisotropic myocardium (on the concave surface) that is aligned along the length and transitions between coiled and un-coiled states during spontaneous myocyte contraction. In this configuration, the muscular-thin-film 26''' transitions from a rolled to an unrolled state and undergoes repeated, cyclic contractions without the need for external pacing. This self pacing is likely due to stretch-activated ion channels that are triggered by the dramatic mechanical deformations.

For each construct type, a schematic is given of the shape 25', 25", and 25''' prior to release from the cover slip with anisotropic myocyte alignment indicated by the lines. Side profiles demonstrate the 3D conformation the films adopt upon release from the cover slip, and the direction of film bending is indicated by the arrows. The video stills show (a) the film strip 26' in a relaxed state at time 0.00 seconds in FIG. 8A; (b) the film strip 26" in a contracted state at 0.60 seconds in FIG. 8B; and (c) the film strip 26''' in both states at 0.60 seconds and at 0.000 seconds, respectively in FIG. 8C. Scale bars in each of the images are 1 mm.

Muscular contraction is more rapid than relaxation, which is driven by the restorative elastic force of the polydimethylsiloxane. This is clearly demonstrated by high-aspect-ratio rectangular strips 26''' with myocyte on the concave surface and aligned along the length (as shown in FIG. 8C).

Figure 9A:
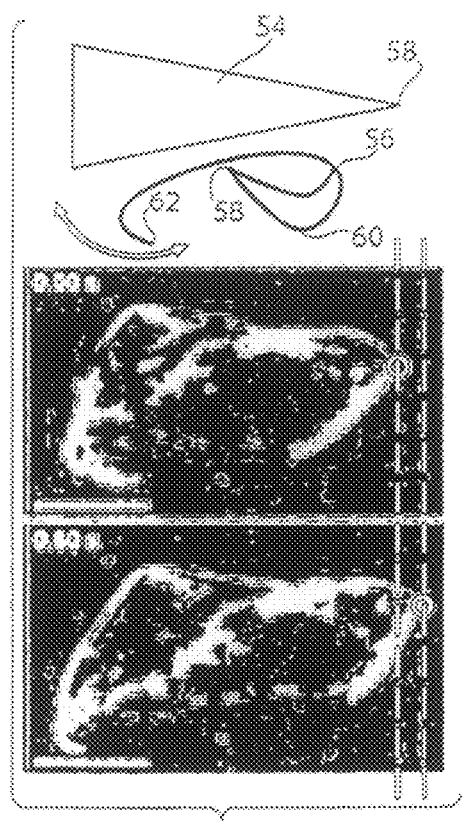
FIG. 9 provides illustrations, images and charts for a myopod formed from a triangular muscular thin film.
Figure 9B:
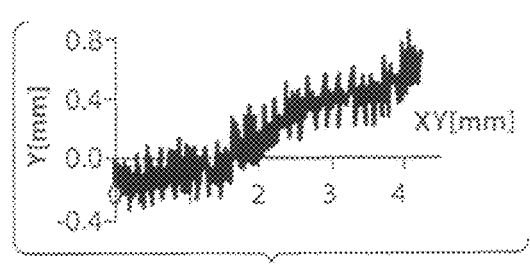
Figure 9C:
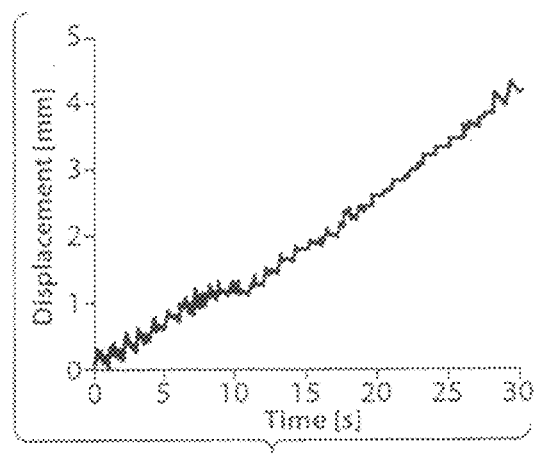

In FIG. 9A, a myopod is formed from a triangular muscular thin film 54 with isotropic myocardium (on the convex surface) by manually folding it into a 3D conformation 56 to break symmetry. Though the muscular thin film is originally in the shape of an isosceles triangle 54, tweezers are used to fold the tip 58 of the triangle 54 (from the right, as shown in FIG. 9A underneath half way along the triangle height. The room-temperature-cured polydimethylsiloxane is hydrophobic and sticks to itself in aqueous solution, providing a convenient way to fabricate complex 3D conformations. This forms an angled footpad 60 that slides in only one direction because of the angle of contact, maintaining directed motion under the propulsive force from pushing steps from the rest of the triangle via displacement of the leg 62. The schematic of FIG. 9A illustrates the shape of the triangle 54 prior to release from the cover slip, with isotropic myocardium indicated by uniform shading. The side profile demonstrates the manually formed 3D conformation 56 after release, and the direction of film bending is indicated by the arrows. Analysis of video frames shows that the myopod walked across the bottom of the Petri dish by extending its rear leg 62 from a relaxed (0.00 s) to contracted (0.60 s) state. The chart of FIG. 9B tracks the front of the myopod to show consistent, directed locomotion along a constant direction when paced at 1 Hz and 20 V at (C) an average speed of about 8 nm/min. Scale bars are 1 mm.

Figure 10A:
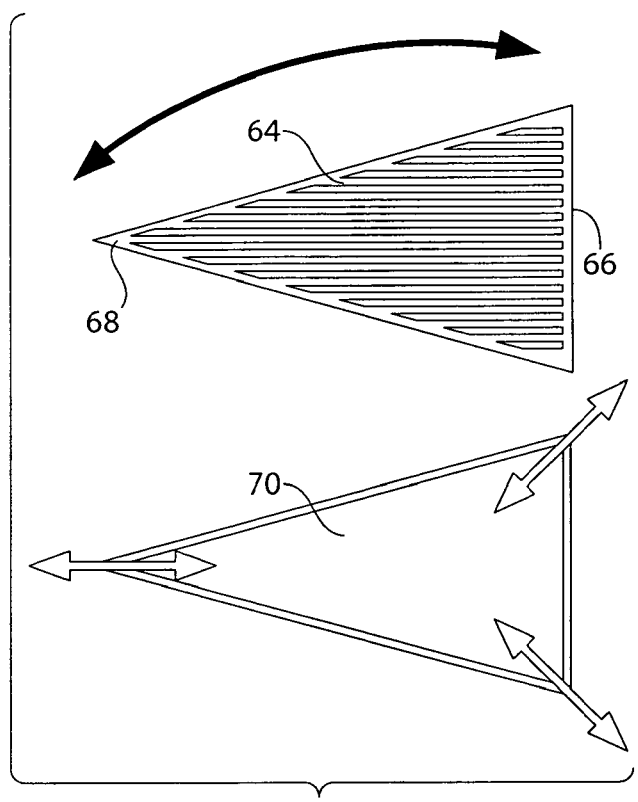
FIG. 10 provides illustrations of myopods formed from a triangular muscular thin film.

In FIG. 10, a triangle swimmer 64 utilizes multi-scale symmetry breaks in order to replicate anguilliform aquatic swimming. The symmetry breaks, in combination, generate directed propulsive thrust during contraction, thus serving as a simplistic model for aquatic locomotion. Directed motion is achieved via a break of spatiotemporal symmetry, marking the transition from motility to mobility by mimicking the shape and muscular organization of aquatic creatures, such as the eel. By varying spatial organization of the muscular thin film through the shape of the polydimethylsiloxane-substrate and muscle-tissue architecture, the spatial requirements of mobility are achieved. In the triangle swimmer 64, the polydimethylsiloxane film is about 30 µm thick, with the muscular thin film cut into an isosceles triangle with the anisotropic myocardium aligned along the height (horizontally, as shown in the top illustration in FIG. 10A), generating contraction along this axis only. This shape results in decreasing stiffness from the base 66 to the tip 68 of the triangle 64 so that the myocardium along the height of the triangle 64 maximizes the strain developed in order to flap the triangle tip 68 like a tail. This isosceles triangle shape of the muscular thin film is utilized to break symmetry. A similarly sized rectangle with myocytes aligned along the length (as shown in FIG. 7) oscillates in place.

Figure 10B:
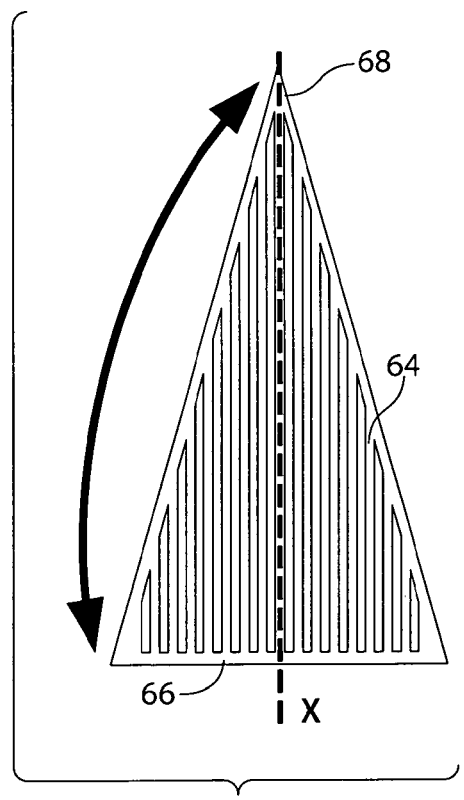

The motions of similarly shaped triangle swimmers with anisotropic (triangle 64) versus isotropic (triangle 70) 2D myocardium and paced at 1 Hz, 20 V are illustrated in FIG. 10A. Distinct differences in mobility were demonstrated. When both constructs were started at the same point, the anisotropic triangle swimmer moves farther than does the isotropic triangle swimmer after 13 seconds. Tracking both swimmers 64 and 70 showed that the anisotropic swimmer 64 is about five times faster than the isotropic swimmer 70. The muscular-thin-film anisotropic triangle swimmer 64 is realized by aligning myocytes parallel to a non-symmetry axis (i.e., the height), of the triangle. The myocyte alignment is indicated in FIG. 10B by the lines; and the direction of film bending is indicated by the arrows, which denote the points that bend down, into the plane of the paper upon myocyte contraction. Tracking the triangle swimmer 64 during contraction through subsequent video frames showed that the relaxed construct contracted by pulling the tail (tip) on the triangle in towards the base. As the myocytes relaxed, the triangle returned to it original shape, producing a propulsive force that drives the construct forward. The triangle's swimming velocity is a function of pacing rate. Spontaneous contractions produced 0.5 to 0.75 mm displacements spaced sporadically in time. Pacing at 0.5 Hz, 1.0 Hz, and 2.0 Hz produced cyclic contractions that reveal a peak in swimming velocity of about 24 mm/min at 1.0 Hz pacing.

The shape of the muscular thin film, alone, is not enough to enable swimming locomotion. Comparing similar triangle swimmers, one 64 with isotropic and the other 70 with anisotropic myocardium (FIG. 10A), demonstrates that tissue microarchitecture, specifically the increased uniaxial strain and force of anisotropic tissue, generates propulsion. Over the time of 13 seconds, the anisotropic swimmer 64 traveled about 5 times farther in a constant direction and at a rate of 3 mm/min compared to the isotropic swimmer 70, which drifted to the side at a rate of 0.3 mm/min. Furthermore, the path of the isotropic swimmer 70 is random compared to the directed motion of the anisotropic swimmer 64.

External pacing of the triangle swimmer can be used to maximize swimming velocity, i.e., to break temporal symmetry. To maximize velocity, the swimmer needs to be constantly moving. If the frequency is too low, the swimmer will stop between contraction strokes; if the frequency is too high, contraction will repeat before a complete stroke, causing the swimmer to twitch in place. A 'sweet spot' in pacing rate was found at 1 Hz pacing to achieve a swimming velocity of 24 mm/min for the muscular-thin-film triangle swimmer. In terms of biological relevance, mechanical efficiency of swimming, determined by slip, is 0.024, an order of magnitude below that generated by bio-robotic fish and eels, but still impressive for a macroscale device powered by a single monolayer of myocytes.

Muscular thin films represent a robust technique for generating engineered 2D myocardium on free-standing polydimethylsiloxane (PDMS) elastomer films with widespread application in soft robotics, tissue engineering and the study of cardiac biomechanics. A number of soft robotic actuators have been demonstrated that evidence a variety of process and application parameters that can be controlled to produce unique functionality, including bending, twisting, linear translation, rotation, grasping, pumping, walking and swimming. These capabilities can be leveraged to build more advanced soft robotic devices by borrowing biological design principles from organisms, such as octopi, that employ elastic, muscular appendages for complex movements. The octopus arms can simulate articulated joints and even produce bipedal locomotion using peripheral motor programs that do not require a brain to function. In addition, myocytes provide impressive, built-in control systems that tap into the high-density chemical energy within glucose molecules to power ATP synthesis; automatically self assemble into monolayers with electrical continuity; and regulate contraction based on external stimuli, such as electrical stimulation, mechanical perturbation and drug interactions. Muscular thin films are dependent on a viable source of myocytes for fabrication, posing a potential issue for mass production because some muscle types, such as cardiac, do not divide and thus require a primary animal source. As a result, muscular thin films scaled up for large production are based on mammalian skeletal muscle or on cardiac myocytes from organisms, such as the Zebra fish, both of which represent muscle tissue that can replicate in vivo and in vitro.

Figure 11:
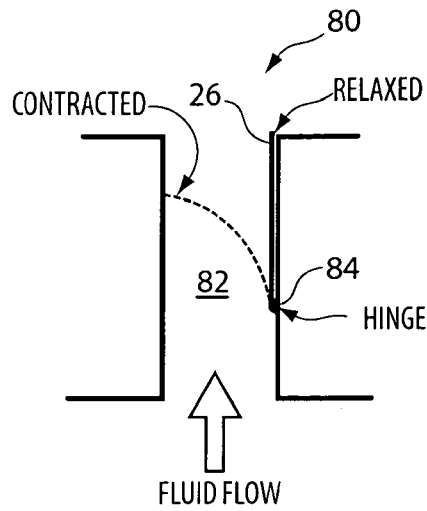
FIGS. 11-13 depict biological micro-control devices and their uses as valves and/or switches in microfluidic systems.
Figure 12:
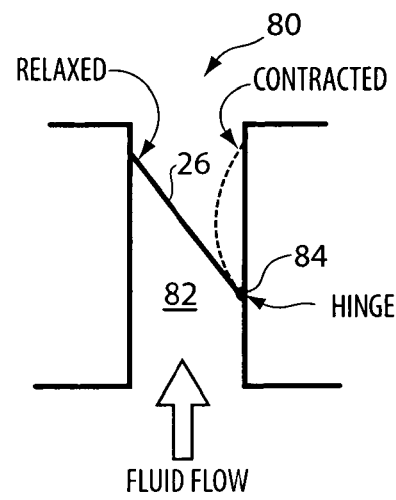
Figure 13:
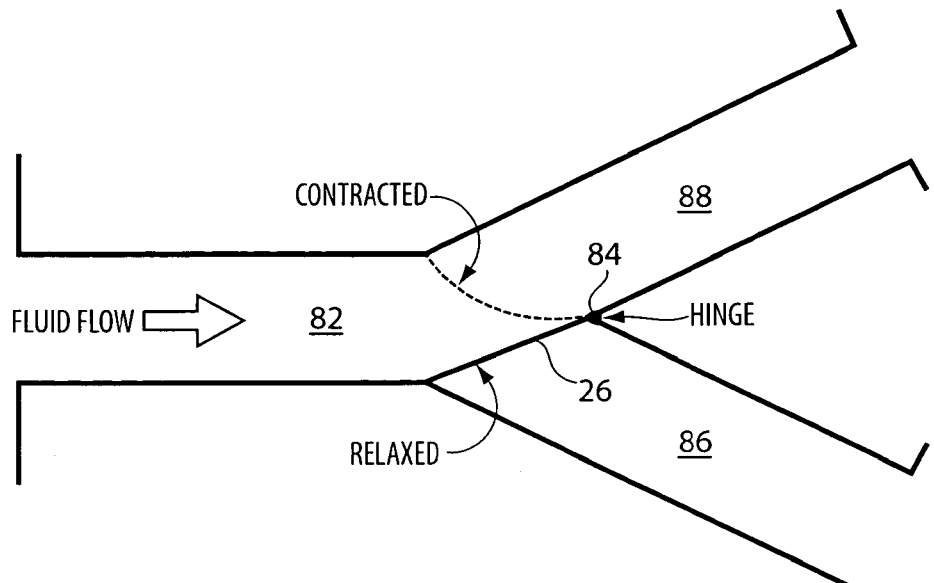

The muscular thin films produced via the methods described herein can be employed in a wide variety of applications. In a first set of embodiments, shown in FIGS. 11-13, the muscular thin film 26 is mounted at one end (acting as a hinge) 84 and serves as a valve (or switch) 80 in a microfluidics device. The muscular thin film 26 is mounted in a fluid-flow passage 82 and is configured to close the passage 82 either in its contracted state (as shown in FIG. 11) or in its relaxed state (as shown in FIG. 12) and to leave the passage 82 open in its opposite state. Accordingly, the valve 80 can be designed to have a default open or closed design based on the selected orientation for the muscular thin film 26 in its relaxed state. In the embodiment of FIG. 13, the muscular thin film 26 is mounted as a switch at a branch for directing fluid flow. As shown, the muscular thin film 26 in its relaxed state will block the passage 86 to the lower right and redirect fluid incoming from the passage 82 to the left into the upper passage 88 on the right. When the muscular thin film 26 (with the muscles tissue on the top side of the film) contracts, it will curve upward to close off the upper passage 88 and direct fluid flow into the now-open lower passage 86. The relaxed and contracted states of the muscular thin films 26 are controlled by external stimulation or in response to a stimulus directly from the fluid. An example of a stimulus from the fluid is the presence of a muscle relaxant in the fluid, which can be utilized, for example, in a lab-on-chip device (e.g., as a smart valve therein) or in a vascular dilator (based on the therapeutic agent).

In another embodiment, the muscular thin film is similarly used as a door, hatch or cover for compartments in, e.g., a lab-on-chip device, wherein the compartment covered by the muscular thin film in its relaxed state contains a composition to negate the effects of a drug or other composition of interest, and wherein the muscular thin film will contract when exposed to the composition of interest, thereby releasing the countering composition. For example, the muscular thin film can be designed to contract and thereby provide access to a compartment in which a vascular dilator is contained when the muscular thin film is exposed to a vasoconstrictor.

In yet another embodiment, the muscular thin film (particularly when rolled in a circular tube) is used as a pump, wherein contraction or relaxation of the film displaces a fluid. In still other embodiments, the muscular thin film can be in the form of a walker or swimmer, as previously discussed; and it can be attached to an object to be transported. Accordingly, the walker or swimmer serves as a propeller or paddle for the object to which it is attached. The swimmer, in fact, can be mounted to the object and configured to operate in the same manner as a fin on a fish, wherein the flapping of the swimmer propels the affixed object through a fluid.

The muscular thin film can also be used in auditory applications. In one embodiment, a thin film coated with heart muscles is tuned to contract and thereby send a signal upon exposure to a specific auditory signal. The muscular thin film, in other embodiments, is used as a biomimetic sensory system. For example, the muscular thin film serves as a tactile sensory system for robotics, wherein the muscular thin film contracts in response to exposure to a physical stimulus, such as movement of an organism or object thereon or there against. Where the muscular thin film is structured as a gripper, the film can collapse around and contain or grasp the object or organism.

Further still, the muscular thin film can be used in a cell-based analog computer, wherein the film is coupled with a source of a stimulus, such as electrical potential or strain. The muscular thin film puts out a signal (much like flipping a switch) when exposed to the stimulus, and it serves as a force amplifier that will respond, e.g., to a small strain with a much larger contraction.

A muscular thin film in the form of an elastic sheet graft material also is used to bind muscle tissue and to provide a conduit for tissue regeneration and/or enhanced function. The graft can be permanent or biodegradable over time. Further, the graft either adheres to muscle on both sides or it has both an adhesive and a non-adhesive side. The graft is in the form of precut/shaped pieces for specific applications, and it is provided in the form of a peel-off sheet for custom cutting of specific-sized films for targeted applications. The graft can operate as a passive device, or it can be dynamically actuated to augment the function of a host tissue. The graft can also serve as a template for anisotropic (patterned) growth of regenerated tissue and is suitable for traumatic injury or wasting diseases.

The muscular thin film, in one embodiment, is implanted and affixed to the eye to serve as a replacement for eye muscles.

In other embodiments, shown in FIGS. 14-19, the muscular thin film is used as an external wound dressing. An elastomer, such as PDMS, is used as the flexible polymer. Thin-film PDMS is fabricated in the form of a cuff 90 (via, e.g., spin coating on a drum) or a wrap (ribbon). A micropatterned extracellular-matrix protein is applied to the PDMS layer to direct the growth of fibroblast and immune cells (to enhance healing and minimize scarring) and/or is loaded with antibiotics to fight infection.

Figure 14:
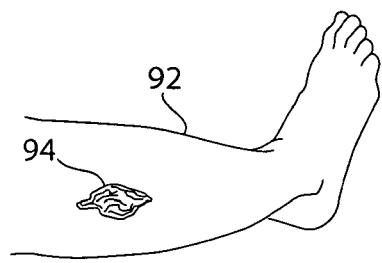
FIGS. 14-19 depict application of a muscular thin film in the form of an external cuff or wrap for wound dressings, and its use to seal gun-shot wounds and as a temporary sealant for severed appendages.
Figure 15:
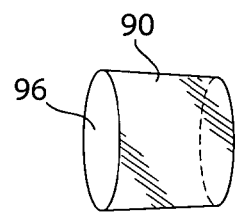
Figure 16:
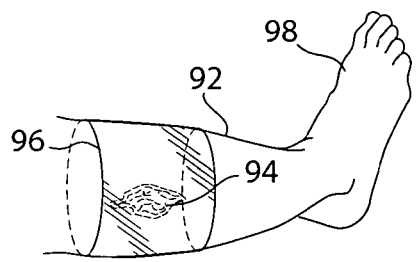

For example, as shown in FIGS. 14-16, the wound dressing can be applied to a limb 92 suffering from a gun-shot wound 94 (as shown in FIG. 14) after actions are taken to control the bleeding and clean the injury site, if possible. The wound dressing, in this example, is in the form of an elastic cuff 90 (shown in FIG. 15) with an interior surface 96 coated with a treatment, such as a layer of antibiotics. The elastic cuff 90 is stretched and slid over the patient's foot 98 and placed over the wound 94 (as shown in FIG. 16). Alternatively, instead of a cuff, a wrap of the same material can be utilized and wrapped around the limb at the wound site in the same manner that an ACE bandage is applied. The wrap can, accordingly, be applied to cover a broader variety of body and wound shapes.

Figure 17:
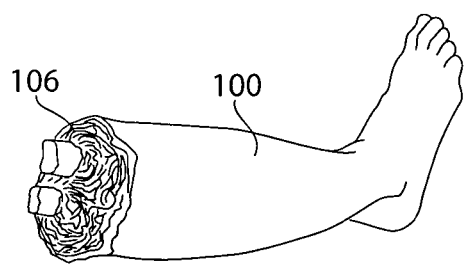
Figure 18:
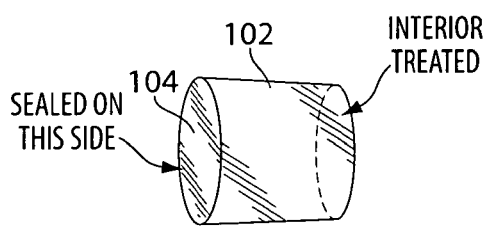
Figure 19:
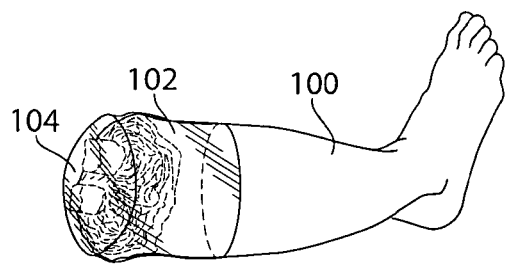

In another example, shown in FIGS. 17-19, the muscular thin film is used as a temporary seal to protect a severed appendage. A severed portion of a leg 100, as shown in FIG. 17, is first cleaned; and the muscular thin film, in the form of a cuff 102 having a sealed end 104 and an internally treated surface (e.g., treated with antibiotics) is slid over the severed end 106 of the appendage to seal it (as shown in FIG. 19). PDMS is oxygen permeable to allow respiration; however, the severed limb 100 is iced to prolong its viability for reattachment. The same type of cuff 102 is also applied to the patient after bleeding is controlled and the injury site is cleaned. The sealed cuff 102 is slid over the severed end of the portion of the appendage still attached to the body.

In still another embodiment, shown in FIGS. 20-25, a muscular thin film is used as a graft for repair and regeneration of soft or hard tissue. The mechanical properties of the film are matched to the mechanical properties of the tissue, and the selection of the surface chemistry is dependent on the role of graft. The selected surface chemistry either promotes cell adhesion and directs cell growth or prevents cell attachment to avoid surgical adhesions. The film may or may not be biodegradable depending on the tissue type, support need, and regenerative capacity.

Figure 20:
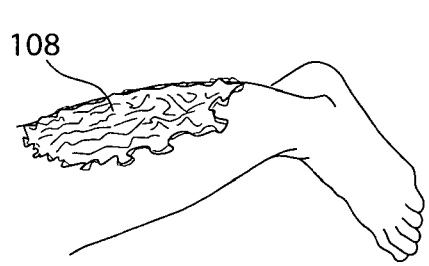
FIGS. 20-25 depict application of a muscular thin film as a graft for repair and/or regeneration of hard and/or soft tissue and its use for fusing and regrowing traumatic muscle injury and as a scaffold to fill voids in muscle tissue.
Figure 21:
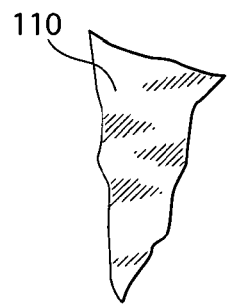
Figure 22:
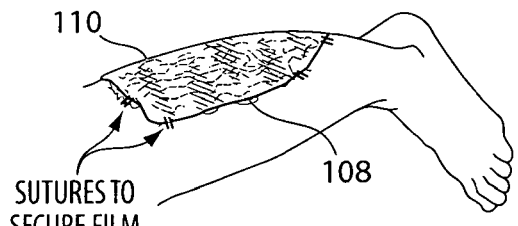

For example, the muscular thin film can be applied as a graft for repairing and regenerating traumatic injured muscle. A traumatically injured calf 108 is shown in FIG. 20. In this case, an elastic graft 110 that can stretch with the regrowth muscle is attached. As shown in FIG. 21, the graft 110 is a PDMS film patterned with extracellular-matrix proteins on both sides to adhere and direct aligned growth of the skeletal muscle cells and tissue fragments (loaded with antibiotics). The muscular thin film graft 110 is implanted in the calf 108 at the site of the traumatically-injured muscle and sutured to the existing muscle, as shown in FIG. 22; and the wound is closed after the film graft 110 is implanted.

Figure 23:
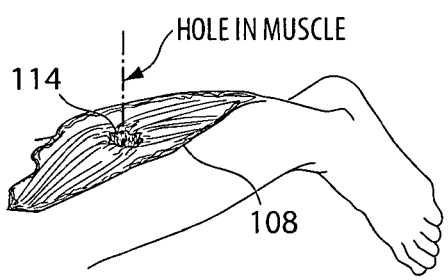
Figure 24:
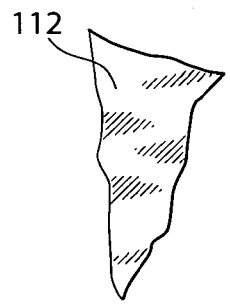
Figure 25:
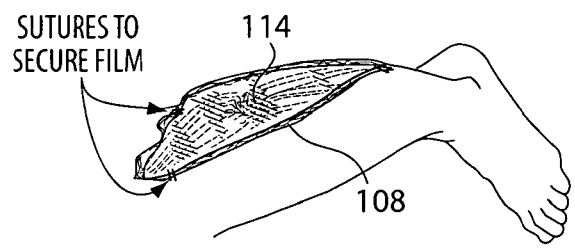

In another example, shown in FIGS. 23-25, the muscular thin film is used as a graft 112 for repairing and regenerating muscle voids, where the patient has a hole 114 in the muscle due, e.g., to injury, cancer, etc. The graft 112 is a PDMS film treated with extracellular-matrix protein and growth factors on one side and with a non-adhesive material (e.g., pluronics, polyethylene oxide, etc.) on the other side. Alternatively, PDMS can be replaced by any comparable elastomer such as polyurethane, thermoplastic elastomers, etc.

Evaluation of Contractile Function and Drug Screening

Figure 26:
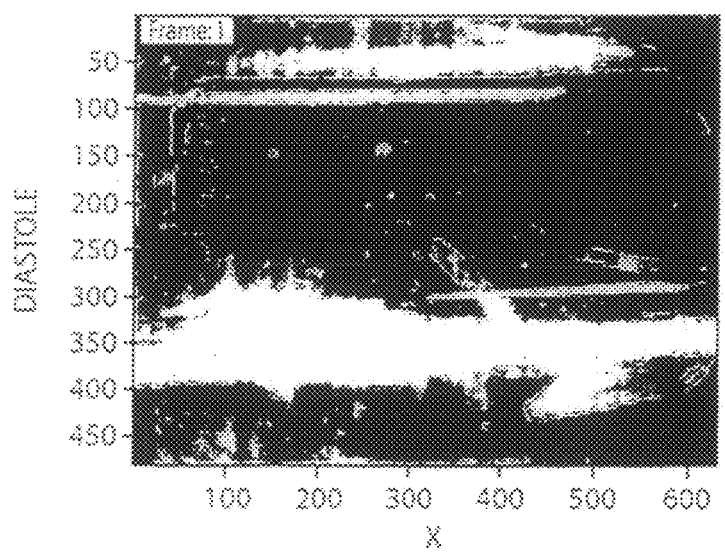
FIG. 26 shows a rectangular-shaped muscular thin film with myocytes anisotropically aligned along its length, wherein the muscular thin film is clamped at one end in a PDMS block.
Figure 27:
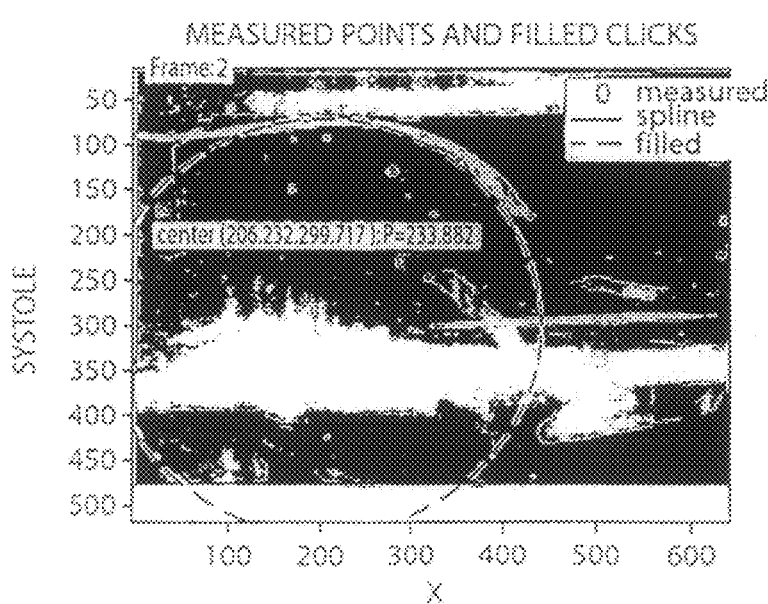
FIG. 27 shows the clamped muscular thin film of FIG. 26, with the myocytes contracted to produce a radius of curvature in the muscular thin film.

Contractile function of muscle cells is evaluated as follows. The use of a muscular thin film to measure contractility of 2D myocardium is shown in FIGS. 26 and 27. For example, the muscular thin film is shaped into a rectangle with myocytes anisotropically aligned along the length. The muscular thin film is clamped at one end in a PD MS block. The clamped muscular thin film, with the myocytes in a relaxed state and with the muscular thin film correspondingly substantially planar, is shown in FIG. 26. When the myocytes contract, they bend the muscular thin film, as shown in FIG. 27. Because the mechanical properties of the PDMS are known, the stress generated by the myocyte during contraction is determined by measuring the radius of curvature of the muscular thin film; as shown in FIG. 27, image processing software is used to assist in finding the radius of curvature, wherein a circle with the radius of curvature is illustrated with a dashed line. This apparatus is useful as a bench top system for investigating contractility in muscular thin films that simulate disease states (myopathies) or the effect of pharmacologic therapies. For example, the films are used to determine the difference in contractility of different myopathies, for drug screening, and to determine how drugs influence contractility of normal muscle and myopathies. This procedure can be used with 2D muscle made of cardiomyocytes, smooth muscle cells or skeletal muscle.

For drug screening, the muscle cells (muscular thin film) are contacted with a candidate compound. For example, the muscular thin film is immersed in a bath of media containing the drug and the effect of the drug on muscle function is measured. Alternatively, the muscular thin film is bathed in a medium containing a candidate compound, and then the cells are washed, prior to measuring muscle function. The cells seeded onto the film are normal muscle cells (cardiac, smooth, or skeletal muscle cells), abnormal muscle cells (e.g., those derived from a diseased tissue, or those that are physically or genetically altered to achieve a abnormal or pathological phenotype or function), or normal cells that are seeded/printed onto the film in an abnormal or aberrant configuration. In some cases, both muscle cells and neuronal cells are present on the film. Evaluation of muscle function includes determining the degree of contraction, i.e., the degree of curvature or bend of the muscular film, and the rate or frequency of contraction/rate of relaxation compared to a normal control or control film in the absence of the candidate compound. An increase in the degree of contraction or rate of contraction indicates that the compound is useful in treatment or amelioration of pathologies associated with myopathies such as muscle weakness or muscular wasting. Such a profile also indicates that the agent is useful as a vasocontractor. A decrease in degree of contraction or rate of contraction indicated that the compound is useful vasodilator and as a therapeutic agent for muscle or neuromuscular disorders characterized by excessive contraction or muscle thickening that impairs function.

Compounds evaluated in this manner are useful in treatment or amelioration of the symptoms of muscular and neuromuscular pathologies such as those described below. Muscular Dystrophies include Duchenne Muscular Dystrophy (DMD) (also known as Pseudohypertrophic), Becker Muscular Dystrophy (BMD), Emery-Dreifuss Muscular Dystrophy (EDMD), Limb-Girdle Muscular Dystrophy (LGMD), Facioscapulohurneral Muscular Dystrophy (FSH or FSHD) (Also known as Landouzy-Dejerine), Myotonic Dystrophy (MMD) (Also known as Steinert's Disease), Oculopharyngeal Muscular Dystrophy (OPMD), Distal Muscular Dystrophy (DD), and Congenital Muscular Dystrophy (CMD). Motor Neuron Diseases include Amyotrophic Lateral Sclerosis (ALS) (Also known as Lou Gehrig's Disease), Infantile Progressive Spinal Muscular Atrophy (SMA, SMA1 or WH) (also known as SMA Type 1, Werdnig-Hoffman), Intermediate Spinal Muscular Atrophy (SMA or SMA2) (also known as SMA Type 2), Juvenile Spinal Muscular Atrophy (SMA, SMA3 or KW) (also known as SMA Type 3, Kugelberg-Welander), Spinal Bulbar Muscular Atrophy (SBMA) (also known as Kennedy's Disease and X-Linked SBMA), Adult Spinal Muscular Atrophy (SMA). Inflammatory Myopathies include Dermatomyositis (PM/DM), Polymyositis (PM/DM), Inclusion Body Myositis (IBM). Neuromuscular junction pathologies include Myasthenia Gravis (MG), Lambert-Eaton Syndrome (LES), and Congenital Myasthenic Syndrome (CMS). Myopathies due to endocrine abnormalities include Hyperthyroid Myopathy (HYP™), and Hypothyroid Myopathy (HYPO™). Diseases of peripheral nerves include Charcot-Marie-Tooth Disease (CMT) (Also known as Hereditary Motor and Sensory Neuropathy (HMSN) or Peroneal Muscular Atrophy (PMA)), Dejerine-Sottas Disease (DS) (Also known as CMT Type 3 or Progressive Hypertrophic Interstitial Neuropathy), and Friedreich's Ataxia (FA). Other Myopathies include Myotonia Congenita (MC) (Two forms: Thomsen's and Becker's Disease), Paramyotonia Congenita (PC), Central Core Disease (CCD), Nemaline Myopathy (NM), Myotubular Myopathy (MTM or MM), Periodic Paralysis (PP) (Two forms: Hypokalemic—HYPOP—and Hyperkalemic—HYPP) as well as myopathies associated with HIV/AIDS. The methods and films are also useful to identify therapeutic agents to treat or ameliorate the symptoms of metabolic muscle disorders such as Phosphorylase Deficiency (MPD or PYGM) (Also known as McArdle's Disease), Acid Maltase Deficiency (AMD) (Also known as Pompe's Disease), Phosphofructokinase Deficiency (PFKM) (Also known as Tarui's Disease), Debrancher Enzyme Deficiency (DBD) (Also known as Cori's or Forbes' Disease), Mitochondrial Myopathy (MITO), Carnitine Deficiency (CD), Carnitine Palmityl Transferase Deficiency (CPT), Phosphoglycerate Kinase Deficiency (PGK), Phosphoglycerate Mutase Deficiency (PGAM or PGAMM), Lactate Dehydrogenase Deficiency (LDHA), and Myoadenylate Deaminase Deficiency (MAD). In addition to the disorders listed above, the screening methods are used to identify agents to reduce vasospasms, heart arrhythmia, cardiomyopathy.

Vasodilators identified as described above are used to reduce hypertension and compromised muscular function associated with atherosclerotic plaques. Smooth muscle cells associated with atherosclerotic plaques are characterized by an altered cell shape and aberrant contractile function. Such cells are used to populate a thin film, exposed to candidate compounds as described above, and muscular function evaluated as described above. Those agents that improve cell shape and function are useful to treat or reduce the symptoms of such disorders.

Smooth muscle cells and/or striated muscle cells line a number of lumen structures in the body, such as airways, gastrointestinal tissues (e.g., esophagus, intestines), and urinary tissues. The function of smooth muscle cells on thin films in the presence and absence of a candidate compound is evaluated as described above to identify agents that increase or decrease the degree or rate of muscle contraction to treat or reduce the symptoms associated with a pathological degree or rate of contraction. For example, such agents are used to treat gastrointestinal motility disorders.

Exemplification a. Substrate Fabrication

Polydimethylsiloxane (PDMS) thin film substrates were fabricated via a multi-step spin coating process. Poly(N-isopropylacrylamide) (PIPAAM) (Polysciences, Inc.) was dissolved at 10 wt % in 99.4% 1-butanol (w/v) and spun coat onto the glass cover slips. Sylgard 184 (Dow Corning) polydimethylsiloxane (PDMS) elastomer was mixed at a 10:1 base to curing agent ratio and spun coat on top of the PIPAAm coated glass cover slip. Polydimethylsiloxane-coated cover slips were then cured.

b. Fibronectin Isotropic and Anisotropic Patterning

The polydimethylsiloxane thin films were coated with either an isotropic or anisotropic layer of fibronectin (FN). In each case, immediately prior to fibronectin treatment, the polydimethylsiloxane-coated cover slips were UV ozone treated for 8 minutes to sterilize the surface and increase hydrophilicity. All subsequent processing was performed in a biohood under sterile conditions. Isotropic fibronectin was deposited by placing a 1 mL lens of 25 μg/mL fibronectin in sterile deionized (DI) water on the polydimethylsiloxane and incubating for 15 minutes. Following incubation, excess fibronectin was removed by washing 3 times with DI water and then air dried prior to cardiomyocyte seeding within 3 hours.

Anisotropic patterning of fibronectin was performed using microcontact printing (μCP). The basic μCP technique is well established and allows the rapid patterning of biomolecules on a variety of planar substrates using polydimethylsiloxane stamps. The variation employed here used a polydimethylsiloxane stamp to pattern fibronectin on the polydimethylsiloxane coated glass cover slips to form anisotropic 2D myocardium. Fibronectin was transferred from the stamp to the polydimethylsiloxane thin film by making conformal contact for 1 minute.

c. Cardiomyocyte Seeding and Culture

Neonatal rat ventricular myocytes were isolated from 2-day old neonatal Sprague-Dawley rats based on published methods. Cells were diluted to a concentration of ~350,000 per mL in seeding media (SM) (M199 media supplemented with 10% FBS), and 3 mL was seeded on each cover slip. After 24 hours incubation, the cover slips were washed 3 times with phosphate buffered saline (PBS) to remove non-adherent cells and recovered with SM. After an additional 24 hours, the media was exchanged with maintenance media (MM) [M199 media supplemented with 2% fetal bovine serum (FBS)] to minimize growth of fibroblasts inevitably present in the primary harvest cardiomyocyte population.

d. Creating Shapes, Releasing them and Creating 3D Conformations

Polydimethylsiloxane films were ready to be formed into shapes and released from the cover slip once the cardiomyocytes have formed the appropriate 2D myocardium microstructure. The Petri dish was placed on a stereomicroscope with darkfield illumination and shapes are cut by hand using a surgical scalpel to cut through the polydimethylsiloxane thin film. Once the Tyrode's solution cools below 35° C., the PIPAAm layer transitions from a hydrophobic state to a hydrophilic state and begins to dissolve. Once the PIPAAm dissolves, the contraction of the myocytes on the polydimethylsiloxane film pulls the cutout shapes free from the cover slip and into solution. The conformation of polydimethylsiloxane films once they release from the cover slip is dependent on the myocardium microstructure, cutout shape and cure conditions. Polydimethylsiloxane films cured at room temperature and less than 20 μm thick could be further manipulated with tweezers by bending the films and touching the non-myocyte covered sides together.

e. Experimental Testing Parameters (Tyrodes, Pacing, Video Recording)

All actuation and observation of the myocyte-polydimethylsiloxane constructs was carried out at room temperature in Tyrodes solution, exchanged every 30 minutes. The polydimethylsiloxane films cutting, release, spontaneous contraction and pacing were performed on a stereomicroscope with darkfield illumination. Constructs were electrically paced using parallel platinum wire electrodes spaced ~1 cm apart and lowered directly into the center of the Petri dish. An external field stimulator (Myopacer, IonOptix) was used to apply a 20 V, 10 msec duration square wave between the electrodes at pacing rates from 0.1 to 5 Hz for durations of up to 2 minutes.

f. Fixation and Staining

Samples were fixed and stained for immunofluorescent imaging to visualize the tissue microarchitecture. Day 4 samples were removed from the incubator, washed 3 times with PBS and fixed for 15 minutes in 4% paraformaldehyde and 2.5% TritonX-100 in PBS. Samples were stained with a 1:200 dilution of sarcomeric α-actinin monoclonal primary antibody in PBS for 1 hour. Samples were then concurrently stained with 1:200 dilutions of 4',6-Diamidino-2-Phenylindole (DAPI), phalloidin conjugated to Alexa-Fluor 488 and goat anti-mouse conjugated to rhodamine secondary antibody in PBS for 1 hour. Samples were imaged on a Leica DMI 6000B inverted light microscope using epifluorescent illumination and digital captured with a 4 Megapixel CCD camera.

g. Video and Image Analysis

Quantification and analysis of actuator motion was performed using ImageJ (NIH) software. The actuator was then manually tracked through each stack of the frame using the manual tracking plug-in. Tracking results were exported into a text file and converted to time-versus-displacement curves for all constructs and XY paths for swimmers and walkers.

In describing embodiments of the invention, specific terminology is used for the sake of clarity. For purposes of description, each specific term is intended to at least include all technical and functional equivalents that operate in a similar manner to accomplish a similar purpose. Additionally, in some instances where a particular embodiment of the invention includes a plurality of system elements or method steps, those elements or steps may be replaced with a single element or step; likewise, a single element or step may be replaced with a plurality of elements or steps that serve the same purpose. Further, where parameters for various properties are specified herein for embodiments of the invention, those parameters can be adjusted up or down by $\frac{1}{20}^{th}$, $\frac{1}{10}^{th}$, $\frac{1}{5}^{th}$, $\frac{1}{3}^{rd}$, $\frac{1}{2}$, etc., or by rounded-off approximations thereof, unless otherwise specified. Moreover, while this invention has been shown and described with references to particular embodiments thereof, those skilled in the art will understand that various substitutions and alterations in form and details may be made therein without departing from the scope of the invention; further still, other aspects, functions and advantages are also within the scope of the invention. The contents of all references, including patents and patent applications, cited throughout this application are hereby incorporated by reference in their entirety. The appropriate components and methods of those references may be selected for the invention and embodiments thereof. Still further, the components and methods identified in the Background section are integral to this disclosure and can be used in conjunction with or substituted for components and methods described elsewhere in the disclosure within the scope of the invention.

What is claimed is:

1. A method for fabricating a free-standing thin film comprising:
   providing a base layer;
   coating a sacrificial polymer layer on the base layer;
   coating a flexible polymer layer that is more flexible than the base layer on the sacrificial polymer layer;
   depositing a spatially micro-patterned engineered surface chemistry on the flexible polymer layer, wherein said spatially micro-patterned engineered surface chemistry allows for the alignment of cells such that a functional tissue is formed;
   seeding cells on the flexible polymer layer comprising the spatially micro-patterned engineered surface chemistry;
   culturing the cells to form a functional tissue; and
   releasing the flexible polymer layer from the base layer to produce a free-standing thin film comprising the functional tissue on the flexible polymer layer comprising the patterned engineered surface chemistry.

2. The method of claim 1, wherein the base layer has an elastic modulus greater than 1 MPA.

3. The method of claim 1, wherein the base layer is a glass cover slip.

4. The method of claim 1, wherein the sacrificial polymer layer comprises poly(N-Isopropylacrylamide).

5. The method of claim 1, wherein the flexible polymer layer comprises polydimethylsiloxane.

6. The method of claim 1, wherein the cells are selected from the following group: myocytes, neurons, fibroblasts, endothelial cells, and dermal cells.

7. The method of claim 6, wherein the cells are cardiomyocytes.

8. The method of claim 7, wherein the myocytes are aligned to produce an anisotropic tissue.

9. The method of claim 1, wherein the sacrificial polymer layer is coated on the base layer via spin coating.

10. The method of claim 1, wherein the flexible polymer layer is coated on the sacrificial polymer layer via spin coating.

11. The method of claim 1, wherein the sacrificial polymer is non-cross-linked poly(N-Isopropylacrylamide), and wherein the flexible polymer is released by dropping the temperature to 32° C. or less, causing the sacrificial polymer to liquefy.

12. The method of claim 1, wherein the sacrificial polymer is crosslinked N-Isopropylacrylamide, and wherein the flexible polymer is released by dropping the temperature to 32° C. or less, causing the sacrificial polymer to become hydrophilic.

13. The method of claim 1, wherein the sacrificial polymer is an electrically actuated polymer, and wherein the flexible polymer is released by applying an electric potential to the sacrificial polymer.

14. The method of claim 1, wherein the sacrificial polymer is a degradable biopolymer, and wherein the flexible polymer is released by dissolving the sacrificial polymer.

15. The method of claim 1, wherein the engineered surface chemistry comprises an extracellular matrix protein.

16. The method of claim 1, wherein the cultured tissue has a thickness of 200 micrometers or less when the flexible polymer layer is released.

17. The method of claim 1, further comprising cutting the flexible polymer layer and tissue to produce a desired shape.

18. The method of claim 1, further comprising utilizing the thin film as an actuator after release.

19. The method of claim 18, wherein the thin film is actuated via exposure to a biological substance.

20. The method of claim 18, wherein the thin film is externally actuated.

21. The method of claim 1, wherein the thin film is a strip having two ends and wherein the cells are myocytes, the method further comprising actuating the tissue to bring the two ends into contact, enabling the thin film to function as a gripper.

22. The method of claim 1, wherein the thin film is a strip and wherein the cells are myocytes, the method further comprising actuating the tissue to coil or un-coil the strip.

23. The method of claim 1, wherein the cells are myocytes, the method further comprising actuating the tissue to propel the thin film.

24. The method of claim 23, wherein the thin film is folded to provide a symmetry break and wherein the thin film is propelled via a walking locomotion across a surface.

25. The method of claim 24, wherein the thin film is propelled via a swimming locomotion through a liquid.

26. The method of claim 1, the method further comprising mounting the released thin film in a fluid-flow passage and actuating the thin film to open or close a gate for fluid flow.

27. The method of claim 1, the method further comprising mounting the released thin film at a port of a compartment and actuating the thin film to open or close the port of the compartment.

28. The method of claim 1, the method further comprising actuating the thin film to pump a fluid.

29. The method of claim 1, further comprising applying the thin film to injured human tissue after release of the thin film.

30. The method of claim 1, further comprising applying the thin film to a severed appendage after release of the thin film.

31. The method of claim 1, wherein the spatially micropatterned engineered surface chemistry is a biopolymer.

32. The method of claim 1, wherein he spatially micropatterned engineered surface chemistry is selected from the group consisting of an extracellular matrix protein, a growth factor, a lipid, a fatty acid, a steroid, a sugar, a biologically active carbohydrate, a proteoglycan, a glycoprotein, a proteolipid, a glycolipid, a biologically derived homopolymer, a nucleic acid, a hormone, an enzyme, a pharmaceutical, a cell surface ligand, a cell surface receptor, a cytoskeletal filament, a cytoskeletal motor protein, and a hydrophylic polymer.

\* \* \* \* \*